(12) United States Patent
Kunimi et al.

(10) Patent No.: US 7,217,830 B2
(45) Date of Patent: May 15, 2007

(54) ORGANIC SILICON COMPOUND AND METHOD FOR PREPARING THE SAME

(75) Inventors: Nobutaka Kunimi, Tsukuba (JP); Masashi Komatsu, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 27 days.

(21) Appl. No.: 11/153,603

(22) Filed: Jun. 16, 2005

(65) Prior Publication Data
US 2006/0004219 A1    Jan. 5, 2006

(30) Foreign Application Priority Data
Jun. 18, 2004   (JP)   ............... P2004-180713

(51) Int. Cl.
*C07F 7/04* (2006.01)
(52) U.S. Cl. .................................... 556/457
(58) Field of Classification Search ............... 556/457
See application file for complete search history.

(56) References Cited

U.S. PATENT DOCUMENTS 6,222,055 B1 *   4/2001   Wolter et al. ............... 556/413

FOREIGN PATENT DOCUMENTS

JP   2000-12532 A   1/2000

OTHER PUBLICATIONS

Harvey, Vinyldimethylsilyl Ethers as Derivatives for the Characterization of Steriods and Cannabinods by Gas Chromatography Mass Spectrometry, Biomedical Mass Spectrometry, 1980, 7, (5), 211-216.*

No et al., Silicon-containing Derivatives of Polycyclic Hydrocarbons. III. Development of Methods for the synthesis of Adamaan-1-ol alkyl(alkoxy)silylmethyl Ethers, Zhurnal Obshchei Khimii (1981), 51(8), 1812-1814.*

Bertrand et al., First Asymmetric Synthesis of Functionalized Monoaromatic Nonaromatic Silanes from Prochiral Silaethylenes, Nouveau Journal de Chimie 1982, 6(7-8), 381-386.*

Bertrand et al., Asymmetric Induction at Silicon from Prochiral Silaethylenes, Journal of the Chemical Society, Chemical Communications, 1980, (9), 382-383.*

(Continued)

*Primary Examiner*—Thurman K. Page
*Assistant Examiner*—Chukwuma Nwaonicha
(74) *Attorney, Agent, or Firm*—Birch, Stewart, Kolasch & Birch, LLP

(57) ABSTRACT

A compound of the formula (1):

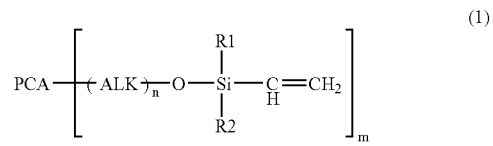

wherein PCA represents a polycycloaliphatic hydrocarbon group, ALK represents a divalent aliphatic hydrocarbon group, m is 1 or 2, n is 0 or 1, and R1 and R2 represent independently each other an alkyl group, an alkenyl group, an alkynyl group, an alkoxy group, an aryl group or an aryloxy group.

4 Claims, 2 Drawing Sheets

OTHER PUBLICATIONS

Chauviere et al., Action of Organometallic on Cyclic and Acyclic Dialkoxysilanes, Journal of Organometallic Chemistry, 1974, 73(3), 305-318.*

Manz et al., Synthesis of Alkylidenephosphiranes by Extrusion of Nitrogen from 3-Alkylidenes-4,5-dihydro-3H-1,2,4-Diazaphospholes, Journal of the Chemical Society, Chemical Communications, 1995, (1), 25-26.*

* cited by examiner

ORGANIC SILICON COMPOUND AND METHOD FOR PREPARING THE SAME

FIELD OF THE INVENTION

The present invention relates to an organic silicon compound useful as a raw material of a polymer film which is preferably used as an interlayer insulation film with a low dielectric constant for insulating multilayer wirings of a semiconductor integrated circuit, and a method for preparing such an organic silicon compound.

PRIOR ART

With the reduction of a circuit size in the designing rule of a semiconductor integrated circuit, a distance between adjacent wirings of the semiconductor integrated circuit has been decreased. As a result, a delay caused by a parasitic capacity between the wirings relatively increases, and the deterioration of a high speed operation performance due to such a delay becomes actual. To cope with this problem, it is required to decrease a capacity between wirings.

To decrease the capacity between wirings, the use of an insulation material with a smaller dielectric constant is studied. Among others, the films of organic polymers are promising as insulation materials with a small dielectric constant, since the organic polymers themselves have a low specific dielectric constant.

For example, JP-A-2000-012532 discloses a method for producing an organic polymer film on the surface of a substrate comprising the steps of vaporizing an organic compound as a raw material, transporting the vaporized compound with a carrier gas, passing the vaporized compound through plasma generated in a reaction chamber under a reduced pressure and spraying it on the surface of the heated substrate to form the organic polymer film thereon.

In the plasma polymerization method described above, the raw material compound is excited to have an increased reactivity while it passes through the plasma, and reaches the surface of the substrate in a state having the increased reactivity. Since the excited raw material compound is polymerized on the substrate, a polymer film formed on the substrate has a backbone reflecting the structure of the raw material compound. Thus, a polymer film can have a different chemical structure when a different compound is used as a raw material for the plasma polymerization method. Accordingly, the physical properties of the polymer film can be remarkably improved by selecting a raw material compound which can provide a chemical structure realizing physical properties required for an interlayer insulation film with a low dielectric constant and polymerizing such a compound by the plasma polymerization method.

Interlayer insulation films with a low dielectric constant are required to have diverse physical properties such as a low specific dielectric constant, high heat resistance, high mechanical strength, good adhesiveness to semiconductive materials, etc. With the recent progress of semiconductor technology, the required properties are sophisticated. To satisfy such requirements, improved control of film quality, that is, the control of a chemical structure in the polymer film is necessary in the production of an organic polymer film by the plasma polymerization method. However, as long as conventional raw materials are used, it may be very difficult to greatly change the chemical structures of the polymer films produced only by the change of film-forming conditions such as a plasma state, a substrate temperature, etc. Therefore, the controllable range of the film quality has its own limits.

Although the plasma polymerization method is advantageous as a method for producing an organic polymer film which can be used as an interlayer insulation film with a low dielectric constant, only a few organic compounds are available as the raw materials of the plasma polymerization method. The further improvement of the dielectric constant of a polymer film obtained is desired.

SUMMARY OF THE INVENTION

An object of the present invention is to provide an organic silicon compound which can be polymerized by plasma polymerization and provide a polymer film having a decreased dielectric constant.

Another object of the present invention is to provide a method for preparing such an organic silicon compound.

Accordingly, the present invention provides a compound of the formula (1):

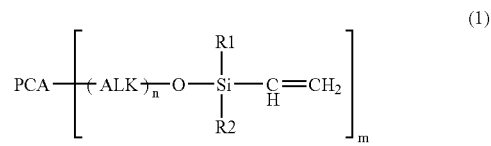

wherein PCA represents a polycycloaliphatic hydrocarbon group having at least 7 carbon atoms, ALK represents a divalent aliphatic hydrocarbon group having 1 to 10 carbon atoms, m is 1 or 2, n is 0 or 1, and R1 and R2 represent independently each other an alkyl group having 1 to 6 carbon atoms, an alkenyl group having 2 to 6 carbon atoms, an alkynyl group having 2 to 6 carbon atoms, an alkoxy group having 1 to 6 carbon atoms, an aryl group having 6 to 10 carbon atoms or an aryloxy group having 6 to 10 carbon atoms.

Furthermore, the present invention provides a method for preparing a compound of the formula (1) comprising the step of reacting a compound of the formula (13) and a compound of the formula (14):

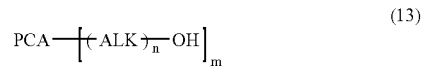

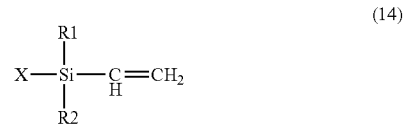

wherein X represents a chlorine atom, a bromine atom, an iodine atom or a tosyl group, and PCA, ALK, m, n, R1 and R2 are the same as defined above.

The organic silicon compound of the formula (1) of the present invention can be polymerized by plasma polymerization, and a polymer film thus produced has a decreased dielectric constant.

DETAILED DESCRIPTION OF THE PREFERRED EMBODIMENTS

Figure 1:
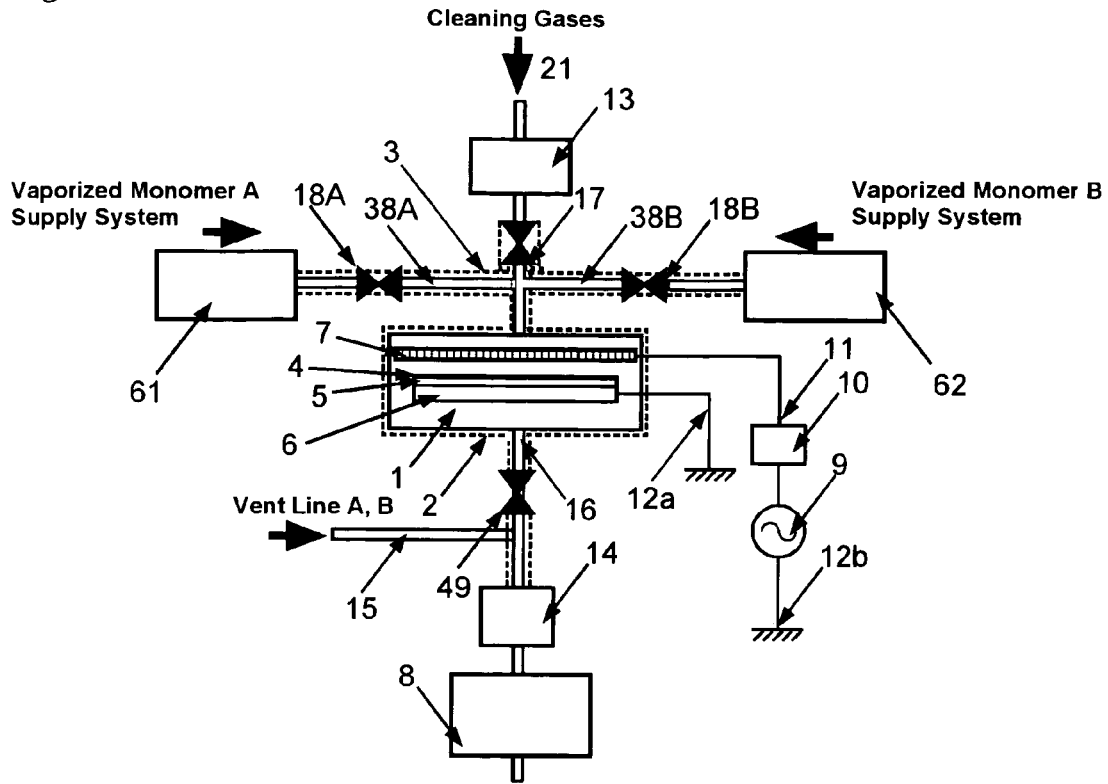
FIG. 1 schematically shows one example of an apparatus for producing a polymer film, which can be used to produce a polymer film according to the present invention.

In the formula (1), PCA represents a polycycloaliphatic hydrocarbon group having at least 7 carbon atoms. When m is 1, PCA is a monovalent polycycloaliphatic hydrocarbon group, while when m is 2, PCA is a divalent polycycloaliphatic hydrocarbon group. PCA may have a carbon-carbon unsaturated bond. PCA is preferably a polycycloaliphatic hydrocarbon group having 7 to 14 carbon atoms, more preferably, 7 to 10 carbon atoms. In particular, PCA is a bicyclo- or tricycloaliphatic hydrocarbon group having 7 to 10 carbon atoms.

Examples of the monovalent polycycloaliphatic hydrocarbon group include bicyclo[2.2.1]hept-1-yl group, bicyclo[2.2.1]hept-2-yl group, bicyclo[2.2.1]hept-7-yl group, bicyclo[2.2.1]hept-2-en-1-yl group, bicyclo[2.2.1]hept-2-en-2-yl group, bicyclo[2.2.1]hept-2-en-5-yl group, bicyclo[2.2.1]hept-2-en-7-yl group, bicyclo[2.2.1]hepta-2,5-dien-1-yl group, bicyclo[2.2.1]hepta-2,5-dien-2-yl group, bicyclo[2.2.1]hepta-2,5-dien-7-yl group, bicyclo[2.2.2]oct-1-yl group, bicyclo[2.2.2]oct-2-yl group, bicyclo[2.2.2]oct-2-en-1-yl group, bicyclo[2.2.2]oct-2-en-2-yl group, bicyclo[2.2.2]octa-2,5-dien-1-yl group, bicyclo[2.2.2]octa-2,5-dien-2-yl group, bicyclo[2.2.2]octa-2,5-dien-7-yl group, bicyclo[2.2.2]octa-2,5,7-trien-1-yl group, bicyclo[2.2.2]octa-2,5,7-trien-2-yl group, bicyclo[4.4.0]dec-1-yl group, bicyclo[4.4.0]dec-2-yl group, bicyclo[4.4.0]dec-3-yl group, bicyclo[4.4.0]dec-2-en-1-yl group, bicyclo[4.4.0]dec-2-en-2-yl group, bicyclo[4.4.0]dec-2-en-3-yl group, bicyclo[4.4.0]dec-2-en-4-yl group, bicyclo[4.4.0]dec-2-en-5-yl group, bicyclo[4.4.0]dec-2-en-6-yl group, bicyclo[4.4.0]dec-2-en-7-yl group, bicyclo[4.4.0]dec-2-en-8-yl group, bicyclo[4.4.0]dec-2-en-9-yl group, bicyclo[4.4.0]dec-2-en-10-yl group, bicyclo[4.4.0]dec-3-en-1-yl group, bicyclo[4.4.0]dec-3-en-2-yl group, bicyclo[4.4.0]dec-3-en-3-yl group, bicyclo[4.4.0]deca-3,8-dien-1-yl group, bicyclo[4.4.0]deca-3,8-dien-2-yl group, bicyclo[4.4.0]deca-3,8-dien-3-yl group, tricyclo[3.3.1.1$^{3,7}$]dec-1-yl group, tricyclo[3.3.1.1$^{3,7}$]dec-2-yl group, etc. Examples of the divalent polycycloaliphatic group are those corresponding to the above-exemplified monovalent groups.

The polycycloaiphatic hydrocarbon group may optionally be substituted with at least one substituent selected from the group consisting of an alkyl group having 1 to 10 carbon atoms, an alkoxy group having 1 to 10 carbon atoms, an acyl group having 1 to 10 carbon atoms, an aryl group having 6 to 10 carbon atoms and an aryloxy group having 6 to 10 carbon atoms. Among these substituents, an alkyl group having 1 to 10 carbon atoms is preferable. In particular, a methyl group, an ethyl group, a n-propyl group, an isopropyl group, a n-butyl group, an isobutyl group, a sec-butyl group or a tert-butyl group is preferable.

Particularly preferable examples of the polycycloaliphatic hydrocarbon group represented by PCA include groups of the formulae (2), (3), (4), (5) and (6):

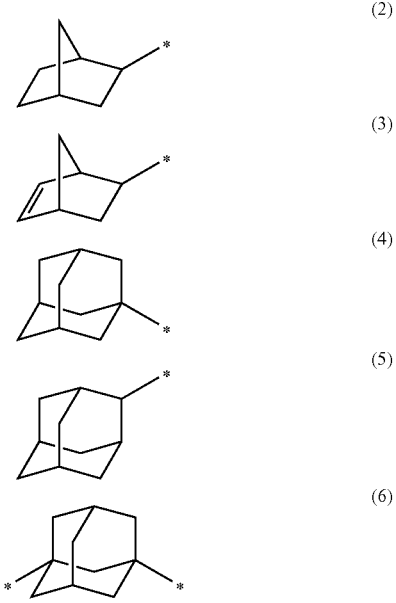

wherein the asterisk * represents a position at which the group bonds to -(ALK)$_n$—.

In the formula (1), ALK represents a divalent hydrocarbon group having 1 to 10 carbon atoms. This divalent hydrocarbon group may be a linear or branched group, or may have an alicyclic moiety and/or an unsaturated bond. When the unsaturated bond is contained, its position may not be limited. Preferably, the hydrocarbon group is a linear or branched aliphatic hydrocarbon group having 1 to 6 carbon atoms and optionally one or more double and/or triple bonds. More preferably, the hydrocarbon group is a linear aliphatic hydrocarbon group having 1 to 4 carbon atoms and optionally a double bond.

Specific examples of the divalent aliphatic hydrocarbon group include a methylene group, an ethylene group, a propylene group, a trimethylene group, a tetramethylene group, a pentamethyene group, a hexamethylene group, a vinylene group, a propenylene group, a butenylene group, a butadienylene group, an ethynylene group, a propynylene group, a butynylene group, a cyclopentylene group, a cyclohexylene group, etc.

The above divalent hydrocarbon group may optionally be substituted with at least one substituent selected from the group consisting of an alkyl group having 1 to 10 carbon atoms, an alkoxy group having 1 to 10 carbon atoms, an acyl group having 1 to 10 carbon atoms, an aryl group having 6 to 10 carbon atoms and an aryloxy group having 6 to 10 carbon atoms. Among these substituents, an alkyl group having 1 to 10 carbon atoms is preferable. In particular, a methyl group, an ethyl group, a n-propyl group, an isopropyl group, a n-butyl group, an isobutyl group, a sec-butyl group or a tert-butyl group is preferable.

Among the divalent hydrocarbon groups represented by ALK, a methylene group, an ethylene group and a vinylene group are particularly preferable.

In the formula (1), R1 and R2 represent independently each other an alkyl group having 1 to 6 carbon atoms, an alkenyl group having 2 to 6 carbon atoms, an alkynyl group having 2 to 6 carbon atoms, an alkoxy group having 1 to 6 carbon atoms, an aryl group having 6 to 10 carbon atoms or an aryloxy group having 6 to 10 carbon atoms.

The alkyl group having 1 to 6 carbon atoms may be a linear or branched one. Specific examples of the alkyl group include a methyl group, an ethyl group, a n-propyl group, an isopropyl group, a n-butyl group, an isobutyl, sec-butyl group and a tert-butyl group.

The alkenyl group having 2 to 6 carbon atoms may be a linear or branched one, and the position of the double bond is arbitrary. Specific examples of the alkenyl group include a vinyl group, an allyl group, an isopropenyl group, a 2-methylvinyl group, a 1-ethylvinyl group, a 2-ethylvinyl group, a 1,2-dimethylvinyl group, a 2,2-dimethylvinyl group, a 3-methylallyl group, an isopropenylmethyl group, etc.

The alkynyl group having 2 to 6 carbon atoms may also be a linear or branched one, and the position of the triple bond is arbitrary. Specific examples of the alkynyl group include an ethynyl group, a propargyl group, a 2-methylethynyl group, an ethynylmethyl group, a 1-ethynylethyl group, a 2-ethynylethyl group, a 2-butynyl group, etc.

The alkoxy group having 1 to 6 carbon atoms may be a linear or branched one. Specific examples of the alkoxy group include a methoxy group, an ethoxy group, a n-propoxy group, an isopropoxy group, a n-butoxy group, an isobutoxy group, a sec-butoxy group, a tert-butoxy, etc.

The aryl group having 6 to 10 carbon atoms may be an aromatic hydrocarbon group or a heterocyclic aromatic group. Examples of the aromatic hydrocarbon group include those having a benzene nucleus, a naphthalene nucleus, an anthracene nucleus, a phenanthrene nucleus, a fluorene nucleus, etc. Examples of the heterocyclic aromatic group include those having a nitrogen-containing heterocyclic ring such as a pyridine ring, a pyrazine ring, an imidazole ring, a pyrrole ring, a triazine ring, a pyrimidine ring, a purine ring, etc., and those having an oxygen- or sulfur-containing heterocyclic ring such as a furan ring, a thiophene ring, etc.

Specific examples of the aryl group include a phenyl group, a naphthyl group, an anthranyl group a fluorenyl group, a pyridinyl group, etc.

An aryloxy group is a group consisting of an aryl group exemplified above and an oxygen atom which is bonded to the aryl group. Specific examples of the aryloxy group include a phenoxy group, a naphthoxy group, etc.

R1 and R2 preferably represent independently each other an alkyl group having 1 to 6 carbon atoms, more preferably 1 to 4 carbon atoms, an alkenyl group having 2 to 6 carbon atoms, more preferably 2 to 4 carbon atoms, an alkynyl group having 2 to 6 carbon atoms, more preferably 2 to 4 carbon atoms, or an alkoxy group having 1 to 6 carbon atoms, more preferably 1 to 4 carbon atoms. In particular, R1 and R2 preferably represent independently each other a methyl group, an ethyl group, a propyl group, an isopropyl group, a vinyl group, an allyl group, an ethynyl group, a propargyl group, a methoxy group or an ethoxy group.

Preferable examples of the compound of the formula (1) include 1-dimethylvinylsiloxy-bicyclo[2.2.1]heptane, 2-dimethylvinylsiloxy-bicyclo-[2.2.1]heptane, 7-dimethylvinylsiloxy-bicyclo[2.2.1]heptane, 1-dimethylvinylsiloxy-bicyclo[2.2.1]hept-2-ene, 2-dimethylvinylsiloxy-bicyclo[2.2.1]hept-2-ene, 5-dimethylvinylsiloxy-bicyclo[2.2.1]hept-2-ene, 7-dimethylvinylsiloxy-bicyclo[2.2.1]hept-2-ene, 1-dimethylvinylsiloxy-bicyclo[2.2.1]hepta-2,5-diene, 2-dimethylvinylsiloxy-bicyclo[2.2.1]hepta-2,5-diene, 7-dimethylvinylsiloxy-bicyclo[2.2.1]hepta-2,5-diene, 1-dimethylvinylsiloxymethyl-bicyclo[2.2.1]heptane, 2-dimethylvinylsiloxymethyl-bicyclo[2.2.1]heptane, 7-dimethylvinylsiloxymethyl-bicyclo[2.2.1]heptane, 1-dimethylvinylsiloxymethyl-bicyclo[2.2.1]hept-2-ene, 2-dimethylvinylsiloxymethyl-bicyclo[2.2.1]hept-2-ene, 5-dimethylvinylsiloxymethyl-bicyclo[2.2.1]hept-2-ene, 7-dimethylvinylsiloxymethyl-bicyclo[2.2.1]hept-2-ene, 1-dimethylvinylsiloxymethyl-bicyclo[2.2.1]hepta-2,5-diene, 2-dimethylvinylsiloxymethyl-bicyclo[2.2.1]hepta-2,5-diene, 7-dimethylvinylsiloxymethyl-bicyclo[2.2.1]hepta-2,5-diene, 1-(2-dimethylvinyl siloxy)ethyl-bicyclo[2.2.1]heptane, 2-(2-dimethylvinylsiloxy)ethyl-bicyclo[2.2.1]heptane, 7-(2-dimethylvinylsiloxy)ethyl-bicyclo[2.2.1]heptane, 1-(2-dimethylvinylsiloxy)ethyl-bicyclo[2.2.1]hept-2-ene, 2-(2-dimethylvinylsiloxy)ethyl-bicyclo[2.2.1]hept-2-ene, 5-(2-dimethylvinylsiloxy)ethyl-bicyclo[2.2.1]hept-2-ene, 7-(2-dimethylvinylsiloxy)ethyl-bicyclo[2.2.1]hept-2-ene, 1-(2-dimethylvinylsiloxy)ethyl-bicyclo[2.2.1]hepta-2,5-diene, 2-(2-dimethylvinylsiloxy)ethyl-bicyclo[2.2.11]hepta-2,5-diene, 7-(2-dimethylvinylsiloxy)ethyl-bicyclo[2.2.1]hepta-2,5-diene, 1-methyldivinylsiloxy-bicyclo[2.2.1]heptane, 2-methyldivinylsiloxy-bicyclo[2.2.1]heptane, 7-methyldivinylsiloxy-bicyclo[2.2.1]heptane, 1-methyldivinylsiloxy-bicyclo[2.2.1]hept-2-ene, 2-methyldivinylsiloxy-bicyclo[2.2.1]hept-2-ene, 5-methyldivinylsiloxy-bicyclo[2.2.1]hept-2-ene, 7-methyldivinylsiloxy-bicyclo[2.2.1]hept-2-ene, 1-methyldivinylsiloxy-bicyclo[2.2.1]hepta-2,5-diene, 2-methyldivinylsiloxy-bicyclo[2.2.1]hepta-2,5-diene, 7-methyldivinylsiloxy-bicyclo[2.2.1]hepta-2,5-diene, 1-trivinylsiloxy-bicyclo[2.2.1]heptane, 2-trivinylsiloxy-bicyclo[2.2.1]heptane, 7-trivinylsiloxy-bicyclo[2.2.1]heptane, 1-trivinylsiloxy-bicyclo[2.2.1]hept-2-ene, 2-trivinylsiloxy-bicyclo[2.2.1]hept-2-ene, 5-trivinylsiloxy-bicyclo[2.2.1]hept-2-ene, 7-trivinylsiloxy-bicyclo[2.2.1]hept-2-ene, 1-trivinylsiloxy-bicyclo[2.2.1]hepta-2,5-diene, 2-trivinylsiloxy-bicyclo[2.2.1]hepta-2,5-diene, 7-trivinylsiloxy-bicyclo[2.2.1]hepta-2,5-diene, 1-dimethylvinylsiloxy-tricyclo[3.3.1.1$^{3,7}$]decane, 2-dimethylvinylsiloxy-tricyclo[3.3.1.1$^{3,7}$]decane, 1-dimethylvinylsiloxymethyl-tricyclo[3.3.1.1$^{3,7}$]decane, 2-dimethylvinylsiloxymethyl-tricyclo[3.3.1.1$^{3,7}$]decane, 1-(2-dimethylvinylsiloxy)ethyl-tricyclo[3.3.1.1$^{3,7}$]decane, 2-(2-dimethylvinylsiloxy)ethyl-tricyclo[3.3.1.1$^{3,7}$]decane, 1-(2-dimethylvinylsiloxy)propyl-tricyclo[3.3.1.1$^{3,7}$]decane, 2-(2-dimethylvinylsiloxy)propyl-tricyclo[3.3.1.1$^{3,7}$]decane, 1-(3-dimethylvinylsiloxy)propyl-tricyclo[3.3.1.1$^{3,7}$]decane, 2-(3-dimethylvinylsiloxy)propyl-tricyclo[3.3.1.1$^{3,7}$]decane, 1-methyldivinylsiloxy-tricyclo[3.3.1.1$^{3,7}$]decane, 2-methyldivinylsiloxy-tricyclo[3.3.1.1$^{3,7}$]decane, 1-methyldivinylsiloxymethyl-tricyclo[3.3.1.1$^{3,7}$]decane, 2-methyldivinylsiloxymethyl-tricyclo[3.3.1.1$^{3,7}$]decane, 1-methyldivinylsiloxy)ethyl-tricyclo[3.3.1.1$^{3,7}$]decane, 2-(2-methyldivinylsiloxy)ethyl-tricyclo[3.3.1.1$^{3,7}$]decane, 1-trivinylsiloxy-tricyclo[3.3.1.1$^{3,7}$]decane, 2-trivinylsiloxy-tricyclo[3.3.1.1$^{3,7}$]decane, 1-trivinylsiloxymethyl-tricyclo[3.3.1.1$^{3,7}$]decane, 2-trivinylsiloxymethyl-tricyclo[3.3.1.1$^{3,7}$]decane, 1-(2-trivinylsiloxy)ethyl-tricyclo[3.3.1.1$^{3,7}$]decane, 2-(2-trivinylsiloxy)ethyl-tricyclo[3.3.1.1$^{3,7}$]decane, 1,3-bis(dimethylvinylsiloxy)-tricyclo[3.3.1.1$^{3,7}$]decane, 1,3-bis(methyldivinylsiloxy)-tricyclo[3.3.1.1$^{3,7}$]decane, 1,3-bis(trivinylsiloxy)-tricyclo[3.3.1.1$^{3,7}$]decane, 1,3-bis(dimethylvinylsiloxymethyl)-tricyclo[3.3.1.1$^{3,7}$]decane, 1,3-bis(methyldivinylsiloxymethyl)-tricyclo[3.3.1.1$^{3,7}$]decane, 1,3-bis(trivinylsiloxymethyl)-tricyclo[3.3.1.1$^{3,7}$]decane, etc.

The compound of the formula (1) of the present invention may be prepared by reacting a compound of the formula (13) with a compound of the formula (14):

  (13)

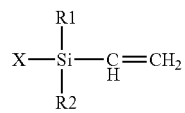  (14)

wherein X represents a chlorine atom, a bromine atom, an iodine atom or a tosyl group, and PCA, ALK, m, n, R1 and R2 are the same as defined above.

An amount of the compound of the formula (14) is stoichiometrically usually from 0.1 to 10 times, preferably from 0.2 to 5 times the amount of the compound of the formula (13).

The above reaction may be carried out in the absence or presence of a solvent. When the solvent is used, a kind of a solvent is not limited. Examples of the solvent include aromatic hydrocarbons such as benzene, toluene, xylene, etc., substituted aromatic hydrocarbons such as chlorobenezene, dichlorobenzene, nitrobenzene, etc., ketones such as acetone, methyl ethyl ketone, methyl isobutyl ketone, etc., nitrites such as acetonitrile, etc., esters such as methyl acetate, ethyl acetate, etc., amides such as dimethylacetamide, dimethylformamide, N-methylpyrrolidone, etc., halogenated hydrocarbons such as dichloroethane, chloroform, carbon tetrachloride, 1,2-dichloroethane, etc., ethers such as diethyl ether, ethyl methyl ether, anisole, tetrahydrofuran, dioxane, etc., and so on. These solvents may be used in admixture. The volume of the solvent may be from 0.2 to 30 times, preferably 0.5 to 20 times the volume of the compound of the formula (13).

To accelerate the above reaction, a base is added to a reaction mixture since an acid HX is generated by the reaction between the compound of the formula (13) and the compound of the formula (14). A kind of a base is not limited. Specific examples of the base include organic bases such as ammonia, trimethylamine, triethylamine, pyridine, imidazole, dimethylaminopyridine, etc., and inorganic bases such as sodium hydroxide, potassium hydroxide, sodium carbonate, potassium carbonate, sodium hydrogen carbonate, potassium hydrogen carbonate, etc. Particularly when a liquid organic base is used, it can also function as a reaction medium. An amount of the base is stoichiometrically usually from 0.2 to 20 times, preferably from 0.5 to 10 times the amount of the acid generated during the reaction.

The order of charging the compound represented by formula (13), the compound of the formula (14), the solvent and the base is not critical.

The reaction temperature is usually from −30 to +250° C., preferably from −10 to +150° C. If the compound of the formula (14) may evaporate at a higher reaction temperature, the reaction can be carried out in a pressure vessel such as an autoclave.

After the completion of the reaction, the desired product can be separated from the reaction mixture and purified by distillation under reduced pressure. If a salt is formed, it can be removed by filtration, or the desired product may be separated from the salt by liquid-liquid extraction with the addition of water or a dilute aqueous solution of an acid (e.g. hydrochloric acid, sulfuric acid, nitric acid, phosphoric acid, acetic acid, etc.) to the reaction mixture.

The compound of the formula (1) prepared by the method described above is used preferably in a high purity form in the production of a polymer film. Thus, the compound of the formula (1) is preferably purified by distillation under conditions selected according to the properties of the compound of the formula (1). The distillation may be carried out under atmospheric pressure or reduced pressure.

When the compound of the formula (1) is used in the production of a polymer film by the plasma polymerization method, the produced polymer film can have a very different internal chemical structure from a polymer film produced using a conventionally used raw material compound alone. Accordingly, the film properties required for an interlayer insulation film with a low dielectric constant can be greatly improved.

The crosslinked structure of the polymer produced from the conventionally used organic compound such as divinylsiloxanebisbenzocyclobutene contains benzene rings, while the polymer film produced from the compound of the formula (1) alone has the backbones including the structure derived from the polycycloaliphatic hydrocarbon groups of the compound of the formula (1) and thus the polymer film has a low specific dielectric constant.

When a polymer film is produced using two or more raw material compounds, the compound other than the compound of the formula (1) is preferably copolymerizable with the compound of the formula (1). When a compound having at least one carbon-carbon unsaturated bond is used as the other compound, the polymer is a copolymer comprising two ore more raw material compounds.

For example, when the compound of the formula (1) and divinylsiloxanebisbenzocyclobutene are used as the raw materials, the carbon-carbon double bond and the benzocyclobutene ring may react each other to form a coplymerized structure of the two compounds in the polymer film. Thus, the film can have the properties specific to the both compounds.

Alternatively, when a compound which alone can be polymerized is used as the other compound, for example, a compound A and a compound B are used as raw materials for the formation of a polymer film, not only they are copolymerized but also each of the compounds A and B is homopolymerized. Thus, when a ratio of the compounds A and B is greatly changed, a copolymer having a composition which reflects the supply ratio of the compounds A and B can be produced, since a local structure emanated from the homopolymerization of the compound A or the compound B can be introduced in the copolymer structure emanated from the copolymerization of the compounds A and B.

When a polymer film is produced using the compound of the formula (1) of the present invention and the other compound, the kind of the other compound is not limited. Preferably, the other compound is one copolymerizable with the compound of the formula (1). For example, a compound having at least one carbon-carbon double or triple bond in a molecule can be copolymerized with the carbon-carbon double bond of the compound of the formula (1). Examples of the compound having at least carbon-carbon double or triple bond include aliphatic hydrocarbons having a vinyl group or an ethynyl group, aromatic hydrocarbons having a vinyl group or an ethynyl group, linear or cyclic siloxane compounds having a vinyl group or an ethynyl group, etc. In particular, a compound of the formula (7) is preferably used:

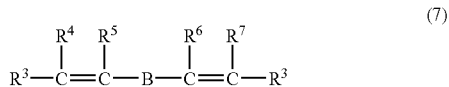

(7)

wherein B is a single bond or a divalent bonding group, two $R^3$ groups represent independently each other a hydrogen atom or a monovalent organic group, and $R^4$ to $R^7$ represent independently each other a hydrogen atom or an aliphatic hydrocarbon group.

Examples of the divalent bonding group represented by B include an aliphatic hydrocarbon group, an aromatic hydrocarbon group, and a group of the formula (8):

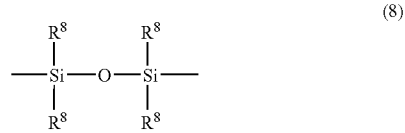

(8)

wherein four $R^8$ groups represent independently each other a hydrogen atom or a methyl group.

The aliphatic hydrocarbon group as a divalent bonding group represented by B may be a linear or branched group, or it may optionally contain an alicyclic moiety. The position of an unsaturated bond is not limited, if present.

The aliphatic hydrocarbon group represented by B is preferably a divalent aliphatic hydrocarbon group having 1 to 10 carbon atoms, more preferably, a linear or branched aliphatic hydrocarbon group having 1 to 6 carbon atoms and optionally at least one double or triple bond, most preferably a linear aliphatic hydrocarbon group having 1 to 4 carbon atoms and optionally a double bond.

Examples of the aromatic hydrocarbon group represented by B include divalent groups having a benzene nucleus, a naphthalene nucleus, an anthracene nucleus, a phenanthrene nucleus, a fluorene nucleus, etc. Specific examples of the aromatic hydrocarbon group include a phenylene group, a naphthylene group, an anthranylene group, a fluolenylene group, etc. Preferably, the aromatic hydrocarbon group is one of these groups.

The aliphatic or aromatic hydrocarbon group represented by B may optionally be substituted by at least one substituent selected from the group consisting of an alkyl group having 1 to 10 carbon atom, an alkoxy group having 1 to 10 carbon atoms, an acyl group having 1 to 10 carbon atoms, an aryl group having 6 to 10 carbon atoms and an aryloxy group having 6 to 10 carbon atoms. The substituent is preferably an alkyl group having 1 to 10 carbon atoms, and in particular, a methyl group, an ethyl group, a n-propyl group, an isopropyl group, a n-butyl group, an isobutyl group, a sec-butyl group or a tert-butyl group is preferable.

B is preferably a single bond, an alkylene group having 1 to 6 carbon atoms, an arylene group having 6 to 10 carbon atoms or a group of the formula (8), more preferably a single bond, a methylene group, an ethylene group, a propylene group, a butylene group, a phenylene or a group of the formula (8) in which all the $R^8$ groups are methyl groups. Among them, a single bond, a phenylene group or a group of the formula (8) in which all the $R^8$ groups are methyl groups is particularly preferable.

The monovalent organic group represented by $R^3$ is preferably a group of the formula (9) or (10):

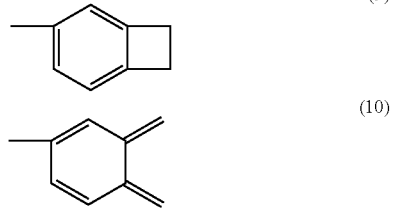

Among them, the group of the formula (9) is most preferable as $R^3$.

Examples of the aliphatic hydrocarbon group represented by $R^4$ to $R^7$ include saturated or unsaturated, linear or branched hydrocarbon groups having 1 to 6 carbon atoms. The position of an unsaturated bond is not limited, if present.

Specific examples of the saturated or unsaturated hydrocarbon group having 1 to 6 carbon atoms include a methyl group, an ethyl group, a n-propyl group, an isopropyl group, a n-butyl group, a isobutyl group, a sec-butyl group, a tert-butyl group, a vinyl group, an allyl group, an ethynyl group, a propargyl group, etc.

$R^4$ to $R^7$ are preferably hydrogen atoms.

Examples of the compound of the formula (7) include 1,3-butadiene, 1,3-divinylbenezene, 1,4-divinylbenzene, methyldivinylbenzene, ethyldivinylbenzene, propyldivinylbenzene, butyldivinylbenzene, a compound of the formula (11) or (12):

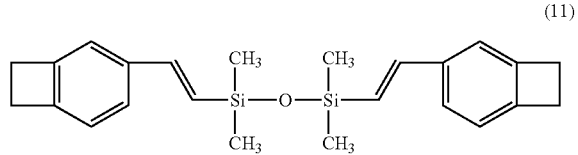

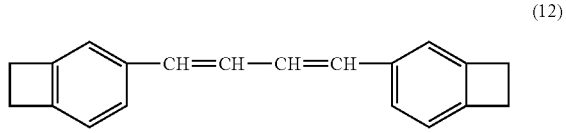

Among them, a compound of the formula (11) is preferable.

Now, one example of an apparatus for producing an polymer film from the compound of the formula (1) of the present invention is explained by making reference to FIG. 1, which schematically shows such an apparatus. Hereinafter, a method for producing a polymer film using two raw materials is explained. However, a polymer film can be produced from a single raw material or three or more raw materials by an analogous method thereto.

In FIG. 1, a reaction chamber 1 is depressurized with a vacuum pump 8, and a substrate-heating member 6 is provided inside the reaction chamber 1. As a base material on which a copolymer film is formed, a semiconductor substrate 5 is fixed to the upper surface of the substrate-heating member 6. Compound A and compound B as raw materials are vaporized in vaporizing supplying systems 61, 62, respectively, and the vapors of compounds A and B are supplied to the reaction chamber 1 together with carrier gasses via vaporized compound-supply pipes 38A, 38B and valves 18A, 18B, respectively. Before reaching the reaction chamber 1, the pipe walls of the pipes 38A, 38B are heated with a heater 3 so that the pipe wall temperatures are maintained at such a temperature that the partial pressures of compounds A and B are always lower than the respective equilibrium vapor pressures thereof at the pipe wall temperature. The vapors of compounds A and B, which are transported with the carrier gas, are supplied to a shower head 7 in the reaction chamber 1 and mixed, and the vapor mixture is sprayed on the surface of the substrate 5. Between the shower head 7 and the substrate-heating member 6, a RF power is applied from a RF power source 9 to induce plasma. Accordingly, the molecules of compounds A and B are excited while they are passing through the plasma generated and then reach the surface of the substrate in the activated state. Then, the molecules are deposited on the surface of the substrate 5 which is heated with the substrate-heating member 6, and the thermal energy is imparted to the already activated molecules of compounds A and B so that they are quickly copolymerized. Consequently, an insulation film 4 of the copolymer comprising compounds A and B grows on the surface of the semiconductor substrate 5.

After compounds A and B, which have been activated with plasma, are adsorbed to a substrate, a part of the molecules of compounds A and B are desorbed. Since this "desorption" and a "polymerization reaction" are competitive, the probability of the desorption is high, if only the thermal process is employed. When plural raw materials are used, the probabilities (or rates) of desorption of the raw materials are different. Therefore, the ratio of the raw materials in the copolymer film should be controlled by adjusting the supply ratio of the raw materials in a wide range by taking the probabilities of desorption of the raw materials into account.

In contrast, in the case of a "plasma polymerization", compounds A and B, which have been activated can be quickly copolymerized when they are adsorbed on the substrate. Thus, the desorption of the molecules of compounds A and B has minimal influence on the composition of the copolymer. Consequently, the ratio of compounds A and B in the copolymer can be easily controlled.

In some cases, during the activation with plasma, a part of the activated raw material compounds may be oligomerized in a gas phase to form dimers, trimers, etc., which are adsorbed on the surface of the substrate. In such cases, since raw material compounds A and B are mixed in an atmosphere under reduced pressure in which the molecules of the compounds have large mobility, the dimers, trimers or oligomers have a composition corresponding to the mixing ratio of compounds A and B in the raw material gas. Accordingly, the insulation film of a copolymer which homogeneously comprises the units derived from compounds A and B can be obtained. When plural raw material compounds having different equilibrium vapor pressures (saturation vapor pressures) with different orders of magnitude, the influence of the difference of the probability of desorption may increase. However, when dimers, trimers or oligomers are formed by intentionally oligomerizing a part of the raw material compounds in the plasma, they have much smaller equilibrium vapor pressure than the monomers, so that the influence of the desorption can be avoided. For example, in a case where the equilibrium vapor pressures of the raw materials are different by about three figures, when the above method is used, the difference of the probabilities of desorption is substantially negligible. In such a case, the distribution of the composition in the insulation film of the copolymer causes no practical problem.

The raw materials are sprayed in the form of a mixed gas on the surface of the substrate. It is necessary for the mixing ratio of the raw materials contained in the mixed gas to be made substantially the same anywhere on the surface of the substrate. The raw materials may be uniformly mixed in the reaction chamber by, for example, mixing them with the shower head 7 placed in the reaction chamber. Alternatively, the raw materials may be uniformly mixed in a passageway before they are introduced in the reaction chamber, and then introduced in the reaction chamber. To uniformly mix the raw materials in the passageway, the flows of the raw materials are combined in a pipe, or a mixing chamber is placed in the apparatus and the raw materials are mixed in the mixing chamber while the materials are retained therein.

The unreacted raw materials do not deposit or condense on the walls of the reaction chamber 1, since the reaction chamber 1 is depressurized with the vacuum pump 8 and the wall of the reaction chamber 1 is heated with a heater 2 like the vaporized compound-supply pipes 38A, 38B. Therefore, the unreacted raw materials in a gas state reach a cold trap 14 via a discharging pipe 16 which is heated with a heater. In the cold trap 14, both raw materials A and B in the gas state condense to liquefy or solidify since the temperature on the inside surface of the cold trap is sufficiently low. As a result, the unreacted raw materials are recovered and removed in the cold trap 14, while the carrier gas from which the raw materials have been removed, that is, the gas utilized to generate the plasma, is transported to the vacuum pump 8.

Figure 2:
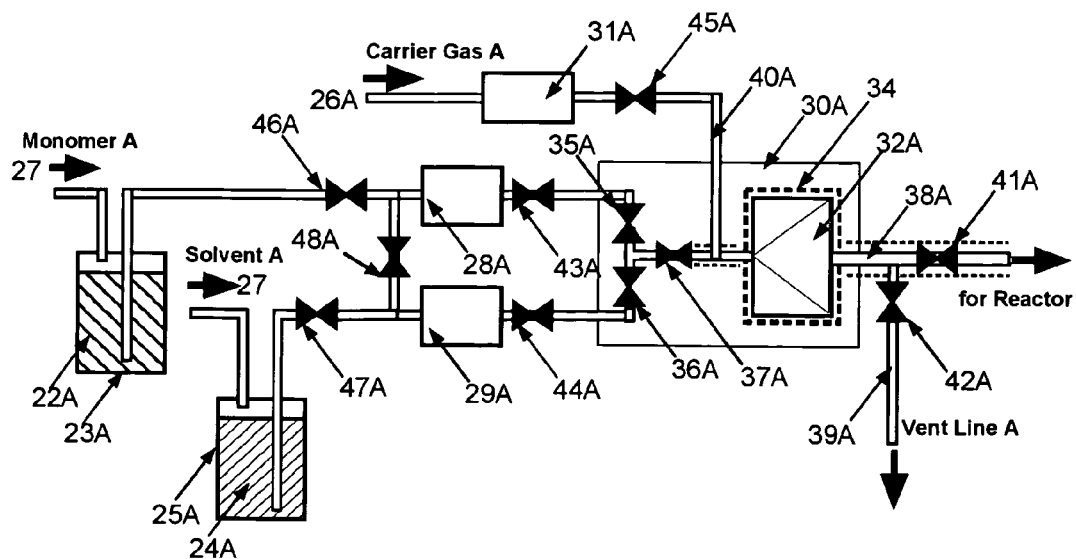
FIG. 2 schematically shows a system for vaporizing a liquid raw material and supplying the vaporized raw material to a reaction chamber together with a carrier gas.

FIG. 2 schematically shows a system for vaporizing a liquid compound and supplying the vaporized compound to the reaction chamber together with a carrier gas, when a compound used to form a polymer film is liquid at room temperature. FIG. 2 shows the flow of the compound (monomer) A from its vaporization in a vaporization controller to just before the supply to the reaction chamber.

The compound 22A is supplied to a vaporization controller 30A via a valve 46A, a liquid flow meter 28A and a valve 43A. Then, compound 22A is supplied to a vaporizing chamber 32A via a vaporization control valve 35A and a valve 37A in the controller, both of which are controlled with feedback signals from the liquid flow meter 28A for the compound 22A. Separately, a carrier gas 26A is supplied to the controller 30A via a valve 45A. Then, the carrier gas 26A and the compound 22A are mixed just upstream the vaporizing chamber 32A. The compound 22A, which is mixed with the carrier gas 26A and supplied to the vaporizing chamber 32A, is continuously vaporized since it is heated with a thermal energy generated with a heater 34 and also the vaporizing chamber 32A is depressurized. That is, the cooling of the compound 22A, which is caused by a thermal energy consumed as a heat of evaporation and the volume expansion of the carrier gas due to the sudden drop of the pressure, is compensated with a thermal energy supplied by heating with the heater 34. Therefore, the vaporized compound 22A is heated to a sufficiently high temperature and then supplied to the reaction chamber 1 via the vaporized compound-supply pipe 38A and the valve 18A which are heated with the heater 3.

When the compounds used in the production of a polymer film are solids, a suitable vaporizing-supplying system may be selected as in the case of the liquid compounds.

As explained above, the compounds, which may be liquid or solid at room temperature, can be supplied in the gas state to the reaction chamber with quickly changing a supply rate to a desired rate by choosing a suitable vaporizing supplying system. If the compounds, which are in the gas state at room temperature, can be used, they may be supplied in the same manner as in the case of supplying conventional raw material gases.

The carrier gas used in the method of the present invention may be any gas inert to the compound(s) to be mixed, for example, helium gas, argon gas, neon gas, etc.

To control the production of the polymer film, other hydrocarbon gas such as methane, ethane, propane, butane, ethylene, propene, acetylene, allene, etc. may be added to the raw material compounds.

EXAMPLES

The present invention will be illustrated by the following examples, which do not limit the scope of the present invention in any way.

Example 1

2-Tricyclo[3.3.1.1$^{3,7}$]decanol (25 g), triethylamine (28 g) and toluene (250 g) were charged in a four-necked 500 ml flask, and then chlorodimethylvinylsilane (30 g) was dropwise added to the mixture at 40° C. over one hour while well stirring. The mixture was stirred at 40° C. for 7 hours with monitoring the progress of the reaction by gas chromatography. After the completion of the reaction, a 4% hydrochloric acid (300 ml) was added to the reaction mixture, and then the mixture was separated. The organic layer was washed with water and concentrated by evaporating off toluene contained in the organic layer, and the residue was distilled under reduced pressure to obtain 2-dimethylvinylsiloxy-tricyclo[3.3.1.1$^{3,7}$]decane having the following structure (40 g):

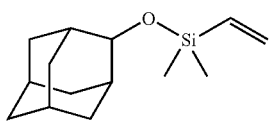

Example 2

1-Dimethylvinylsiloxy-tricyclo[3.3.1.1$^{3,7}$]decane having the following structure:

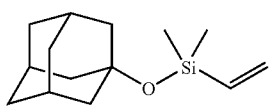

was prepared in the same manner as in Example 1 except that 1-tricyclo[3.3.1.1$^{3,7}$]decanol was used in place of 2-tricyclo[3.3.1.1$^{3,7}$]decanol and the reaction was carried out at 80° C. for 24 hours while stirring.

Example 3

1-Dimethylvinylsiloxymethyl-tricyclo[3.3.1.1$^{3,7}$]decane having the following structure:

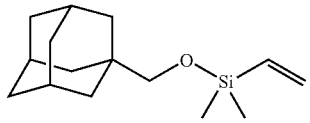

is prepared in the same manner as in Example 1 except that 1-hydroxymethyl-tricyclo[3.3.1.1$^{3,7}$]decane is used in place of 2-tricyclo[3.3.1.1$^{3,7}$]decanol.

Example 4

2-Methyldivinylsiloxy-tricyclo[3.3.1.1$^{3,7}$]decane having the following structure:

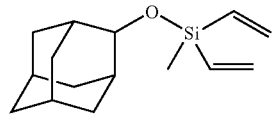

is prepared in the same manner as in Example 1 except that chloromethyldivinylsilane is used in place of chlorodimethylvinylsilane.

Example 5

2-Trivinylsiloxy-tricyclo[3.3.1.1$^{3,7}$]decane having the following structure:

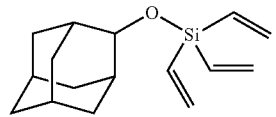

is prepared in the same manner as in Example 1 except that chlorotrivinylsilane is used in place of chlorodimethylvinylsilane.

Application Example 1

This Application Example explains a method for producing a polymer film using only 2-dimethylvinylsiloxy-tricyclo[3.3.1.1$^{3,7}$]decane (as compound A), which was prepared in Example 1.

In the initial state of the vaporization controller of the apparatus for forming a polymer film (FIGS. 1 and 2), the valves 37A, 41A and 49 are "opened", while the valve 18B is "closed", and the reaction chamber 1, discharge pipe 16, effluent pipe 15, vaporizing chamber 32A and vaporized compound-supply pipe 38A are evacuated with the vacuum pump 8.

An vaporizing temperature is preferably a high temperature sufficient for attaining a required supply amount of compound A, but should not be so high as to cause any denaturation such as decomposition or polymerization of compound A, and the clogging of the pipes due to such denaturation in the pipes through which compound A to be vaporized is transported to the vaporizing chamber. The pipes such as the vaporized compound-supply pipe 38A and the like, which are heated with the heater 3, should be made of materials which can withstand such a heating temperature, or the heating temperature is selected so that the pipe materials can withstand such a heating temperature. The temperatures of the pipes being heated are monitored with thermocouples attached to various positions of the pipes, and the outputs of the heaters for heating the pipes are controlled so that the temperatures of the pipes are maintained in preset temperature ranges. Then, the valve 45A of the vaporizing-supplying system shown in FIG. 2 is "opened", and the carrier gas 26A (e.g. helium gas) is supplied to the vaporization controller 30A via a carrier gas-supplying pipe 40A using a gas flow-controller 31A, and further flowed to the reaction chamber 1 via the vaporized compound-supply pipe 38A and the valve 18A. Finally, the mixture of the unreacted compound A and the carrier gas is discharged outside the reaction chamber with the vacuum pump 14 via the discharge pipe 16. In this step, the vaporizing temperature is set to 80° C. The flow rate of the helium carrier gas is adjusted at 500 sccm. Under such conditions, the total pressure P in the vaporization controller is 7 Torr, and the internal pressure of the reaction chamber 1 is 2.0 Torr. The silicon substrate 5 (semiconductor substrate) on which an integrated circuit is printed is heated at 400° C. with the substrate heater 6 placed in the reaction chamber 1. The substrate temperature during the formation of a polymer film is preferably in the range from 200° C. to 450° C.

With the organic monomer-vaporizing supplying system 61 shown in FIG. 2, the vaporized compound A is supplied together with the carrier gas to the reaction chamber 1 via the vaporized compound-supply pipe 38A. The mixed gas containing compound A is distributed with the shower head 7 in the reaction chamber 1 and sprayed on the surface of the substrate 5.

To the shower head 7, a RF powder of 13.56 MHz is applied in relation to the surface of the substrate heater 6 which is grounded. Thereby, the plasma of helium used as the carrier gas is generated below the shower head 7. In this case, the RF powder should have a plasma energy in a level sufficient for only activating compound A. The vaporized compound A is activated while it is sprayed on the substrate 5 through the helium plasma. The preactivated compound A is polymerized on the surface of the substrate 5 which is heated at 200° C. Thereby, a polymer film (an insulation film) is produced on the substrate. In this process, the carrier gas containing the unreacted compound A reaches the discharge pipe 16, and the unreacted compound A is reliquefied (condensed) with the cold trap 14 which is cooled around 20° C. Thus, the unreacted compound A does not get in the vacuum pump 8. Organic compound A is supplied and the formation of the film is continued until the total amount of compound A reaches a predefined amount. Then, the supply of compound A is terminated, and the semiconductor substrate 5 is removed from the reaction chamber.

The polymerization of 2-dimethylvinylsiloxy-tricyclo [3.3.1.1$^{3,7}$]decane may proceed through the crosslinking of the vinyl groups in the molecules. Furthermore, the Si—O—Si bonds may be formed because of the presence of the Si—O bond. In addition to these reactions, reactions involving various radicals derived from the partial structures of the molecules such as vinyl radicals, methyl radicals, tricyclodecyl radicals, etc. may proceed, and such reactions can proceed quickly so that a material having a tricyclodecane structure inside can be formed.

Figure 3:
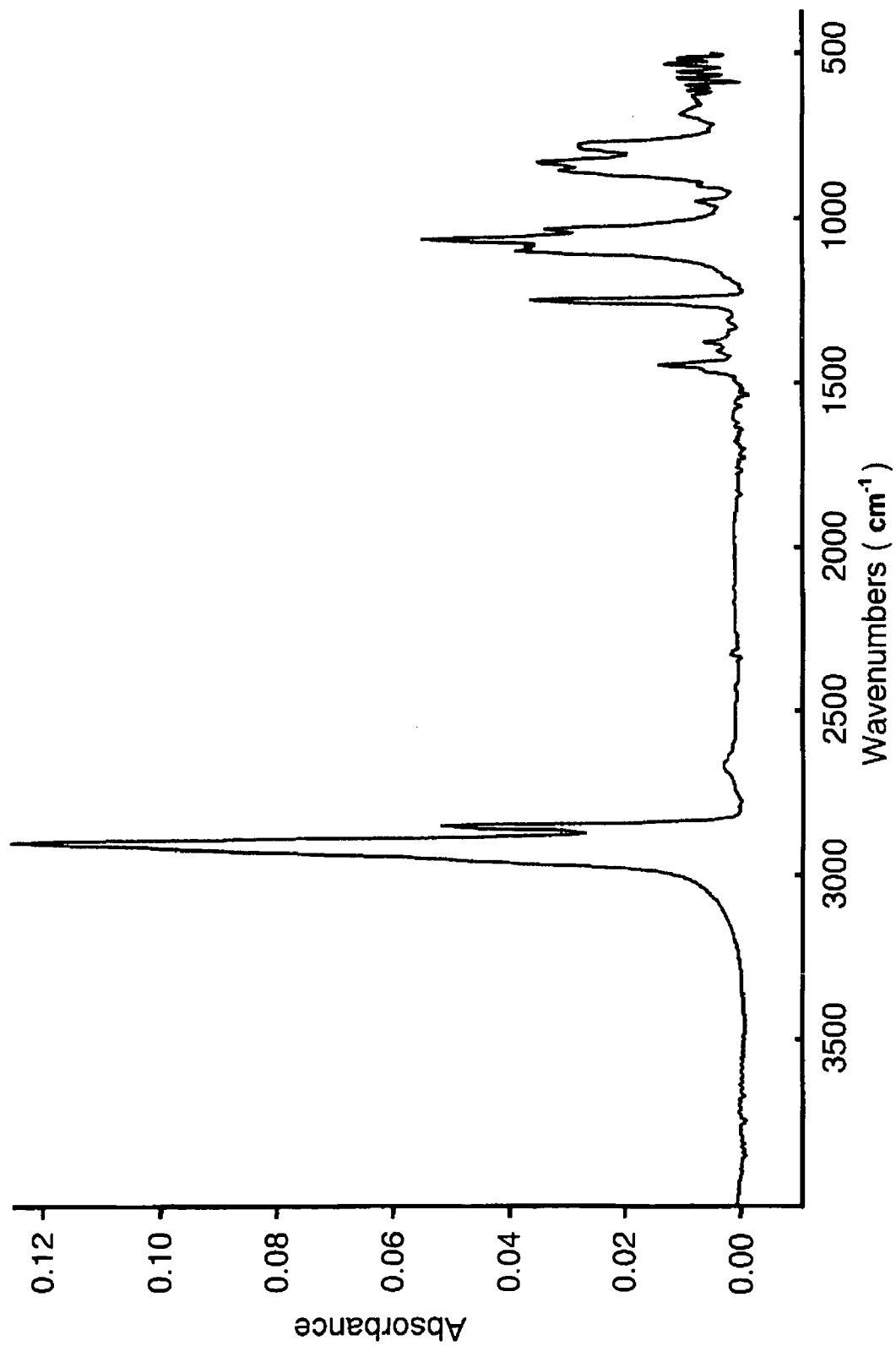
FIG. 3 is the FT-IR chart of the polymer film produced in Application Example 1.

The polymer film produced in Application Example 1 was analyzed by FT-IR. The FT-IR chart obtained is shown in FIG. 3.

Application Example 2

A film of a copolymer comprising raw material compound A and raw material compound B (an insulation film) is produced in the same manner as in Application Example 1 except that 2-dimethylvinylsiloxy-tricyclo[3.3.1.1$^{3,7}$]decane is used as compound A, and the compound of the formula (11) is used as raw material B. Compounds A and B are vaporized with the monomer-vaporizing supplying systems 61 and 62 respectively and then mixed together with helium carrier gas and supplied to the reaction chamber 1 via the vaporized compound-supply pipes 38A, 38B, respectively.

The copolymerization of 2-dimethylvinylsiloxy-tricyclo [3.3.1.1$^{3,7}$]decane and the compound of the formula (11) may proceed such that the benzocyclobutene structure of the compound of the formula (11) is ring-opened to form the 1,2-divinylidene structure, and then the 1,2-divinylidene structure reacts with the vinyl group of 2-dimethylvinylsiloxy-tricyclo[3.3.1.1$^{3,7}$]decane by the Diels-Alder reaction. Thereby, the backbones reflecting the chemical structures of the both raw material compounds can be formed in the film. Therefore, the film produced can have the properties stemmed from the both compounds. For example, the film may have the process compatibility to the multilayer wiring process of a semiconductor circuit while decreasing a specific dielectric constant.

What is claimed is:
1. A compound of the formula (1):

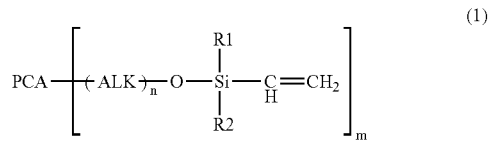

(1)

wherein PCA represents a group of formula (4), (5) or (6);

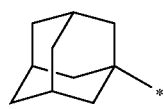

(4)

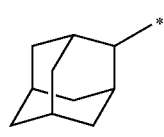

(5)

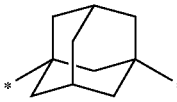

(6)

ALK represents a methylene group, m is 1 or 2, n is 0 or 1, and R1 and R2 represent independently each other a methyl group or a vinyl group, and wherein the asterisk * represents a position at which the group bonds to -(ALK)hd n-.

2. A method for preparing a compound of the formula (1):

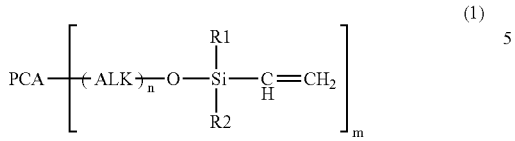  (1)

wherein PCA represents a group of formula (4), (5) or (6);

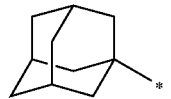  (4)

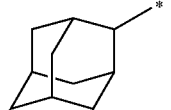  (5)

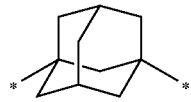  (6)

ALK represents a methylene group m is 1 or 2, n is 0 or 1, and R1 and R2 represent independently each other a methyl group or a vinyl group, and wherein the asterisk * represents a position at which the group bonds to -(ALK)hd n—, comprising the step reacting a compound of the formula (13) and a compound of the formula (14):

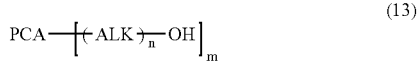  (13)

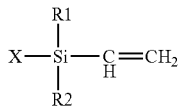  (14)

wherein X represents a chlorine atom, a bromine atom, an iodine atom or a tosyl group, and PCA, ALK, m, n, R1 and R2 are the same as defined above.

3. The method according to claim 2, wherein the reaction is carried out in the presence of a base.

4. The method according to claim 2, or 3, wherein the compound of the formula (1) is recovered by distillation after the reaction of the compound of the formula (13) and the compound of the formula (14).

* * * * *